US008934987B2

(12) United States Patent
Stahmann et al.

(10) Patent No.: US 8,934,987 B2
(45) Date of Patent: Jan. 13, 2015

(54) IMPLANT ASSIST APPARATUS FOR ACOUSTICALLY ENABLED IMPLANTABLE MEDICAL DEVICE

(75) Inventors: Jeffrey E. Stahmann, Ramsey, MN (US); Paul J. Huelskamp, St. Paul, MN (US); Binh C. Tran, Minneapolis, MN (US); Krishna Sridharan, Shoreview, MN (US); Jamie S. Collier, St. Paul, MN (US); Marshall S. Comisar, St. Paul, MN (US); Keith R. Maile, New Brighton, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 435 days.

(21) Appl. No.: 12/496,332

(22) Filed: Jul. 1, 2009

(65) Prior Publication Data

US 2010/0016840 A1 Jan. 21, 2010

Related U.S. Application Data

(60) Provisional application No. 61/080,840, filed on Jul. 15, 2008.

(51) Int. Cl.
*A61N 1/37* (2006.01)
*A61B 5/00* (2006.01)
(Continued)

(52) U.S. Cl.
CPC .......... *A61B 5/0028* (2013.01); *A61N 1/37247* (2013.01); *A61N 1/37252* (2013.01); *A61B 5/0031* (2013.01); *A61N 1/37205* (2013.01);
(Continued)

(58) Field of Classification Search
CPC .......... A61N 1/37247; A61N 1/37252; A61N 1/37217
USPC ................................. 607/30–32, 60
See application file for complete search history.

(56) References Cited

U.S. PATENT DOCUMENTS

| 3,874,388 A | 4/1975 | King et al. |
| 4,391,124 A | 7/1983 | Drost et al. |

(Continued)

FOREIGN PATENT DOCUMENTS

| EP | 0897690 | 2/1999 |
| EP | 0928598 | 8/2000 |

(Continued)

OTHER PUBLICATIONS

International Search Report and Written Opinion issued in PCT/US2009/049409, Nov. 19, 2009, 17 pages.
(Continued)

*Primary Examiner* — Tammie K Heller
(74) *Attorney, Agent, or Firm* — Faegre Baker Daniels LLP (57) ABSTRACT

Devices, systems and methods for delivering and positioning an implantable medical device and for evaluating an acoustic communication link are disclosed. An illustrative system includes a catheter adapted to contain an implantable device with a biosensor and an acoustic transducer configured to transmit an acoustic signal, and an implant assist device in acoustic communication with the implantable device via an acoustic communication link. The implant assist device includes an acoustic transducer adapted to receive the acoustic signal transmitted by the implantable medical device, and control/processing circuitry configured to evaluate a performance of the acoustic link.

18 Claims, 6 Drawing Sheets

(51) Int. Cl.
*A61N 1/372* (2006.01)
*A61N 1/378* (2006.01)

(52) U.S. Cl.
CPC .......... *A61N 1/37217* (2013.01); *A61N 1/3787* (2013.01)
USPC ................ 607/60; 607/31; 607/32

(56) References Cited

U.S. PATENT DOCUMENTS

| | | | |
|---|---|---|---|
| 4,407,296 A | 10/1983 | Anderson | |
| 4,485,813 A | 12/1984 | Anderson et al. | |
| 4,492,107 A | 1/1985 | Sandhu | |
| 4,672,976 A | 6/1987 | Kroll | |
| 4,836,204 A | 6/1989 | Landymore et al. | |
| 4,846,191 A | 7/1989 | Brockway et al. | |
| 4,886,065 A | 12/1989 | Collins, Jr. | |
| 4,900,303 A | 2/1990 | Lemelson | |
| 4,917,089 A | 4/1990 | Sideris | |
| 4,966,148 A | 10/1990 | Millar | |
| 5,040,538 A | 8/1991 | Mortazavi | |
| 5,218,965 A | 6/1993 | Ring | |
| 5,284,138 A | 2/1994 | Kujawski | |
| 5,303,207 A | 4/1994 | Brady et al. | |
| 5,334,217 A | 8/1994 | Das | |
| 5,411,551 A | 5/1995 | Winston et al. | |
| 5,415,630 A | 5/1995 | Gory et al. | |
| 5,451,235 A | 9/1995 | Lock et al. | |
| 5,509,900 A | 4/1996 | Kirkman et al. | |
| 5,604,531 A | 2/1997 | Iddan et al. | |
| 5,634,936 A | 6/1997 | Linden et al. | |
| 5,656,036 A | 8/1997 | Palmaz | |
| 5,662,711 A | 9/1997 | Douglas | |
| 5,704,352 A | 1/1998 | Tremblay et al. | |
| 5,725,552 A | 3/1998 | Kotula et al. | |
| 5,733,249 A | 3/1998 | Katzin et al. | |
| 5,733,294 A | 3/1998 | Forber et al. | |
| 5,733,313 A | 3/1998 | Barreras, Sr. et al. | |
| 5,772,669 A | 6/1998 | Vrba | |
| 5,775,331 A | 7/1998 | Raymond et al. | |
| 5,800,497 A | 9/1998 | Bakels et al. | |
| 5,824,053 A | 10/1998 | Khosravi et al. | |
| 5,833,603 A | 11/1998 | Kovacs et al. | |
| 5,853,005 A | 12/1998 | Scanlon | |
| 5,855,563 A | 1/1999 | Kaplan et al. | |
| 5,860,923 A | 1/1999 | Lenker et al. | |
| 5,891,154 A | 4/1999 | Loeffler | |
| 5,967,980 A | 10/1999 | Ferre et al. | |
| 5,967,986 A | 10/1999 | Cimochowski et al. | |
| 5,967,989 A | 10/1999 | Cimochowski et al. | |
| 5,995,876 A | 11/1999 | Kruse et al. | |
| 6,002,969 A | 12/1999 | Machek et al. | |
| 6,015,386 A | 1/2000 | Kensey et al. | |
| 6,015,387 A | 1/2000 | Schwartz et al. | |
| 6,030,413 A | 2/2000 | Lazarus | |
| 6,033,366 A | 3/2000 | Brockway et al. | |
| 6,053,873 A | 4/2000 | Govari et al. | |
| 6,076,016 A | 6/2000 | Feierbach | |
| 6,077,227 A | 6/2000 | Miesel et al. | |
| 6,097,984 A | 8/2000 | Douglas | |
| 6,106,464 A | 8/2000 | Bass et al. | |
| 6,140,740 A | 10/2000 | Porat et al. | |
| 6,159,156 A | 12/2000 | Van Bockel | |
| 6,179,858 B1 | 1/2001 | Squire et al. | |
| 6,193,745 B1 | 2/2001 | Fogarty et al. | |
| 6,214,025 B1 | 4/2001 | Thistle et al. | |
| 6,231,516 B1 | 5/2001 | Keilman et al. | |
| 6,236,889 B1 | 5/2001 | Soykan et al. | |
| 6,239,724 B1 | 5/2001 | Doron et al. | |
| 6,240,312 B1 | 5/2001 | Alfano et al. | |
| 6,246,898 B1 | 6/2001 | Vesely et al. | |
| 6,277,078 B1 | 8/2001 | Porat et al. | |
| 6,278,790 B1 | 8/2001 | Davis et al. | |
| 6,309,350 B1 | 10/2001 | Van Tassel | |
| 6,328,699 B1 | 12/2001 | Eigler et al. | |
| 6,331,163 B1 | 12/2001 | Kaplan | |
| 6,379,308 B1 | 4/2002 | Brockway et al. | |
| 6,409,674 B1 | 6/2002 | Brockway et al. | |
| 6,416,474 B1 | 7/2002 | Penner et al. | |
| 6,432,050 B1 | 8/2002 | Porat et al. | |
| 6,442,413 B1 | 8/2002 | Silver | |
| 6,447,522 B2 | 9/2002 | Gambale et al. | |
| 6,475,170 B1 | 11/2002 | Doron et al. | |
| 6,486,588 B2 | 11/2002 | Doron et al. | |
| 6,527,780 B1 | 3/2003 | Wallace et al. | |
| 6,543,272 B1 | 4/2003 | Vitek | |
| 6,585,763 B1 | 7/2003 | Keilman et al. | |
| 6,592,553 B2 | 7/2003 | Zhang et al. | |
| 6,628,989 B1 | 9/2003 | Penner et al. | |
| 6,645,143 B2 | 11/2003 | Van Tassel et al. | |
| 6,660,021 B1 | 12/2003 | Palmer et al. | |
| 6,685,638 B1 | 2/2004 | Taylor et al. | |
| 6,699,186 B1 | 3/2004 | Wolinsky et al. | |
| 6,702,847 B2 | 3/2004 | DiCarlo | |
| 6,730,108 B2 | 5/2004 | Van Tassel et al. | |
| 6,738,671 B2 | 5/2004 | Christophersom et al. | |
| 6,743,173 B2 | 6/2004 | Penner et al. | |
| 6,746,404 B2 | 6/2004 | Schwartz | |
| 6,747,916 B1 | 6/2004 | Fleury et al. | |
| 6,755,855 B2 | 6/2004 | Yurek et al. | |
| 6,764,446 B2 | 7/2004 | Wolinsky et al. | |
| 6,783,499 B2 | 8/2004 | Schwartz | |
| 6,800,060 B2 | 10/2004 | Marshall | |
| 6,840,956 B1 | 1/2005 | Wolinsky et al. | |
| 6,855,115 B2 | 2/2005 | Fonseca et al. | |
| 6,868,288 B2 | 3/2005 | Thompson | |
| 6,890,303 B2 | 5/2005 | Fitz | |
| 6,899,729 B1 | 5/2005 | Cox | |
| 6,904,308 B2 | 6/2005 | Frisch et al. | |
| 6,920,347 B2 | 7/2005 | Simon et al. | |
| 6,926,670 B2 | 8/2005 | Rich | |
| 6,934,573 B1 | 8/2005 | Glukhovsky et al. | |
| 6,950,690 B1 | 9/2005 | Meron et al. | |
| 6,958,034 B2 | 10/2005 | Iddan | |
| 6,970,742 B2 | 11/2005 | Mann et al. | |
| 6,972,017 B2 | 12/2005 | Smith et al. | |
| 6,984,205 B2 | 1/2006 | Gazdzinski | |
| 7,001,329 B2 | 2/2006 | Kobayashi et al. | |
| 7,006,858 B2 | 2/2006 | Silver et al. | |
| 7,009,634 B2 | 3/2006 | Iddan et al. | |
| 7,011,671 B2 | 3/2006 | Welch | |
| 7,024,248 B2 | 4/2006 | Penner et al. | |
| 7,033,322 B2 | 4/2006 | Silver | |
| 7,035,684 B2 | 4/2006 | Lee | |
| 7,039,453 B2 | 5/2006 | Mullick et al. | |
| 7,060,038 B2 | 6/2006 | Letort et al. | |
| 7,064,472 B2 | 6/2006 | Pelrine et al. | |
| 7,065,409 B2 | 6/2006 | Mazar | |
| 7,076,305 B2 | 7/2006 | Imran et al. | |
| 7,083,822 B2 | 8/2006 | Brightbill | |
| 7,116,352 B2 | 10/2006 | Yaron | |
| 7,118,529 B2 | 10/2006 | Glukhovsky et al. | |
| 7,118,531 B2 | 10/2006 | Krill | |
| 7,131,986 B2 | 11/2006 | Sirhan et al. | |
| 7,160,258 B2 | 1/2007 | Imran et al. | |
| 7,181,261 B2 | 2/2007 | Silver et al. | |
| 7,198,603 B2 | 4/2007 | Penner et al. | |
| 7,211,045 B2 | 5/2007 | Dala-Krishna et al. | |
| 7,273,457 B2 | 9/2007 | Penner | |
| 7,283,874 B2 | 10/2007 | Penner | |
| 7,308,319 B2 | 12/2007 | Lovett et al. | |
| 7,338,512 B2 | 3/2008 | McGuckin, Jr. et al. | |
| 7,347,868 B2 | 3/2008 | Burnett et al. | |
| 7,392,094 B2 | 6/2008 | Zhang et al. | |
| 7,437,193 B2 | 10/2008 | Parramon et al. | |
| 7,452,334 B2 | 11/2008 | Gianchandani et al. | |
| 7,477,946 B2 | 1/2009 | Tockman et al. | |
| 7,555,351 B2 | 6/2009 | Zhang et al. | |
| 7,744,542 B2 | 6/2010 | Piaget et al. | |
| 7,780,694 B2 | 8/2010 | Palmer et al. | |
| 7,850,708 B2 | 12/2010 | Pal | |
| 7,890,188 B2 | 2/2011 | Zhang et al. | |
| 2002/0045920 A1* | 4/2002 | Thompson | 607/60 |
| 2002/0123672 A1 | 9/2002 | Christophersom et al. | |

(56) References Cited

U.S. PATENT DOCUMENTS

| | | |
|---|---|---|
| 2002/0165601 A1 | 11/2002 | Clerc |
| 2002/0183628 A1 | 12/2002 | Reich et al. |
| 2002/0188207 A1 | 12/2002 | Richter |
| 2003/0114897 A1 | 6/2003 | Von Arx et al. |
| 2003/0139796 A1 | 7/2003 | Sequin et al. |
| 2003/0195606 A1 | 10/2003 | Davidson et al. |
| 2003/0200031 A1 | 10/2003 | Kok |
| 2004/0006377 A1 | 1/2004 | Behm |
| 2004/0054403 A1 | 3/2004 | Israel |
| 2004/0116992 A1 | 6/2004 | Wardle et al. |
| 2004/0147969 A1 | 7/2004 | Mann et al. |
| 2004/0176672 A1 | 9/2004 | Silver et al. |
| 2004/0204744 A1 | 10/2004 | Penner et al. |
| 2004/0215228 A1 | 10/2004 | Simpson et al. |
| 2005/0080472 A1 | 4/2005 | Atkinson et al. |
| 2005/0096702 A1 | 5/2005 | Denker et al. |
| 2005/0115561 A1 | 6/2005 | Stahmann et al. |
| 2005/0124875 A1 | 6/2005 | Kawano et al. |
| 2005/0136385 A1 | 6/2005 | Mann et al. |
| 2005/0149108 A1 | 7/2005 | Cox |
| 2005/0149128 A1 | 7/2005 | Heil, Jr. et al. |
| 2005/0149155 A1 | 7/2005 | Scheiner et al. |
| 2005/0149156 A1 | 7/2005 | Libbus et al. |
| 2005/0154321 A1 | 7/2005 | Wolinsky et al. |
| 2005/0165456 A1 | 7/2005 | Mann et al. |
| 2005/0182387 A1 | 8/2005 | Webler |
| 2005/0209678 A1 | 9/2005 | Henkes et al. |
| 2005/0245840 A1 | 11/2005 | Christopherson et al. |
| 2006/0009818 A1 | 1/2006 | Von Arx et al. |
| 2006/0047205 A1 | 3/2006 | Ludomirsky et al. |
| 2006/0064133 A1 | 3/2006 | Von Arx et al. |
| 2006/0064134 A1 | 3/2006 | Mazar et al. |
| 2006/0064142 A1 | 3/2006 | Chavan et al. |
| 2006/0064143 A1 | 3/2006 | Von Arx et al. |
| 2006/0079740 A1 | 4/2006 | Silver et al. |
| 2006/0089627 A1 | 4/2006 | Burnett et al. |
| 2006/0089694 A1 | 4/2006 | Zhang et al. |
| 2006/0122522 A1 | 6/2006 | Chavan et al. |
| 2006/0136004 A1 | 6/2006 | Cowan et al. |
| 2006/0142819 A1 | 6/2006 | Penner et al. |
| 2006/0149329 A1 | 7/2006 | Penner |
| 2006/0149330 A1 | 7/2006 | Mann et al. |
| 2006/0178586 A1 | 8/2006 | Dobak, III |
| 2006/0206153 A1 | 9/2006 | Libbus et al. |
| 2006/0241735 A1 | 10/2006 | Tockman et al. |
| 2006/0259085 A1 | 11/2006 | Zhang et al. |
| 2006/0287700 A1 | 12/2006 | White et al. |
| 2006/0293741 A1 | 12/2006 | Johnson et al. |
| 2007/0049833 A1 | 3/2007 | Tearney et al. |
| 2007/0060959 A1 | 3/2007 | Salo et al. |
| 2007/0129637 A1 | 6/2007 | Wolinsky et al. |
| 2007/0156126 A1 | 7/2007 | Flaherty |
| 2007/0156205 A1 | 7/2007 | Larson et al. |
| 2007/0162090 A1 | 7/2007 | Penner |
| 2007/0179583 A1 | 8/2007 | Goetzinger et al. |
| 2007/0191904 A1 | 8/2007 | Libbus et al. |
| 2007/0208390 A1 | 9/2007 | Von Arx et al. |
| 2007/0250126 A1 | 10/2007 | Maile et al. |
| 2007/0274565 A1 | 11/2007 | Penner |
| 2007/0282413 A1 | 12/2007 | Tockman et al. |
| 2007/0282415 A1 | 12/2007 | Tockman et al. |
| 2008/0071178 A1 | 3/2008 | Greenland et al. |
| 2008/0071248 A1 | 3/2008 | Delgado et al. |
| 2008/0071339 A1 | 3/2008 | Stalker et al. |
| 2008/0108904 A1 | 5/2008 | Heil |
| 2008/0176271 A1 | 7/2008 | Silver et al. |
| 2008/0275350 A1 | 11/2008 | Liao et al. |
| 2008/0283066 A1 | 11/2008 | Delgado et al. |
| 2009/0054793 A1 | 2/2009 | Nunez et al. |
| 2009/0171274 A1 | 7/2009 | Harlev et al. |
| 2009/0270742 A1 | 10/2009 | Wolinsky et al. |
| 2010/0210923 A1 | 8/2010 | Li et al. |

FOREIGN PATENT DOCUMENTS

| | | |
|---|---|---|
| EP | 1068836 | 1/2001 |
| EP | 1488735 | 6/2007 |
| GB | 2333044 | 7/1999 |
| JP | H(11)-089942 | 4/1999 |
| JP | 2000-507142 | 6/2000 |
| JP | 2001-061790 | 3/2001 |
| JP | 2006-500991 | 1/2006 |
| WO | WO83/03348 | 10/1983 |
| WO | WO99/34731 | 7/1999 |
| WO | WO00/16686 | 3/2000 |
| WO | WO00/59376 | 10/2000 |
| WO | WO01/67989 | 9/2001 |
| WO | WO01/87137 | 11/2001 |
| WO | WO 2004/024034 | 3/2004 |
| WO | WO 2004/110263 | 12/2004 |
| WO | WO 2005/058202 | 6/2005 |
| WO | WO2005/067817 | 7/2005 |
| WO | WO2006/062725 | 6/2006 |
| WO | WO2007/057739 | 5/2007 |
| WO | WO 2007/062299 | 5/2007 |
| WO | WO2007/082115 | 7/2007 |
| WO | 2008002654 | 1/2008 |
| WO | WO2008/034077 | 3/2008 |
| WO | WO2008/057720 | 5/2008 |
| WO | WO 2008/060197 | 5/2008 |
| WO | WO2008/060197 | 5/2008 |
| WO | WO2008/144191 | 11/2008 |
| WO | 2009006610 | 1/2009 |

OTHER PUBLICATIONS

Holmes et al. "SirolimusEluting Stents vs. Vascular Brachytherapy for InStent Restenosis Within BareMetal Stents" JAMA295 (11): 1264-1273 Mar. 15, 2006.

Lanning & Shandas, "Development and Validation of Implantable Sensors for Monitoring Function of Prosthetic Heart Valves: In Vitro Studies", Medical & Biological Engineering & Computing, Jul. 2003, vol. 41, issue 4, pp. 416-424.

Sheth et al. "Subacute Thrombosis and Vascular Injury Resulting From Slotted-Tube Nitinol and Stainless Steel Stents in a Rabbit Carotid Artery Model" Circulation 1996, 94: 1733-1740.

Stone et al. "Paclitaxel-Eluting Stents vs.Vascular Brachytherapy for In-Stent Restenosis Within Bare-Metal Stents" JAMA 295(11): 1253-1263, Mar. 15, 2006.

Webster's II new Riverside University Dictionary, Riverside Publishing Company, 1994, pp. 421 and 625.

Webster's II new Riverside University Dictionary, Riverside Publishing Company, 1994, pp. 722.

Wenaweser et al. "Stent thrombosis following baremetal stent implantation: success of emergency percutaneous coronary intervention and predictors of adverse outcome" European Heart Journal 26: 1180-1187 2005.

Goodall, Eleanor V. et al., "Position-Seletive Activation of Peripheral Nerve Fibers with a Cuff Electrode", IEEE Transactions on Biomedical Engineering, IEEE Service Center, Piscataway, NJ, US, vol. 43, No. 8, Aug. 1, 1996.

International Search Report and Written Opinion issued in PCT/US2010/020756, mailed Sep. 27, 2010.

Invitation to Pay Fees and Partial Search Report issued in PCT/US2010/020756, mailed May 12, 2010.

International Search Report and Written Opinion from PCT/US2008/062229, mailed Jan. 5, 2009.

Triantaphyllou, Evangelos et al., "Development and Evaluation of Five Fuzzy Multiattribute Decision-Making Methods", International Journal of Approximate Reasoning 1996; 14:281-310.

Mullins, C.E. et al., "Implantation of Balloon-Expandable Intravascular Grafts by Catheterization in Pulmonary Arteries and Systemic Veins", Circulation, 1988, vol. 77, pp. 188-199.

\* cited by examiner

IMPLANT ASSIST APPARATUS FOR ACOUSTICALLY ENABLED IMPLANTABLE MEDICAL DEVICE

CROSS-REFERENCE TO RELATED APPLICATION

This application claims the benefit under 35 U.S.C. §119 of U.S. Provisional Application No. 61/080,840, filed on Jul. 15, 2008, entitled "Implant Assist Apparatus For Acoustically Enabled Implantable Medical Device," which is incorporated herein by reference in its entirety for all purposes.

TECHNICAL FIELD

The present invention relates generally to implantable medical devices. More particularly, the present invention relates to devices, systems, and methods for delivering and positioning an implantable medical device at a desired location within a patient's body, and for confirming the adequacy of an acoustic communication link between an implantable medical device and a communicating device.

BACKGROUND

Medical devices that can be implanted within a patient's body for monitoring one or more physiological parameters and/or to provide therapeutic functions are known. For example, implantable medical devices (IMDs) can be placed in the body for monitoring a variety of properties such as temperature, blood pressure, strain, and fluid flow. In some cases, the IMD can be configured to sense other chemical properties, electrical properties, and/or magnetic properties within the body. In addition, implantable medical devices that perform one or more therapeutic functions, such as pacing or defibrillation, are known.

In certain applications, the IMD can be used in conjunction with other devices located inside or outside of a patient's body for performing therapy on the patient. In some applications, for example, an implantable pressure sensor can be used in conjunction with one or more cardiac rhythm management (CRM) devices for predicting the onset of congestive heart failure and delivering an appropriate therapy to a patient. In addition, some implantable sensing devices can also be used for monitoring and treating hypertension, in automatic CRM device settings optimization, and in rhythm discrimination.

Implanting an IMD generally involves delivering and anchoring the IMD at a desired location within the body. In some applications, the placement location and positioning of the IMD may affect the performance of the IMD. For example, the placement location and positioning of the IMD within the body can be important for sensor accuracy, long term stability, and physician acceptance and adoption. In some applications, the placement location and positioning of the IMD within the body may also affect the ability of the IMD to accurately communicate with other implanted devices, or to communicate with an external device. In some cases, it may be useful to confirm the adequacy of the communication link over time in response to changing dynamic conditions within the body. Subsequent to implantation, for example, it may be useful to periodically check the status of the communication link to ensure that the IMD can continue to accurately transmit sensor data and device status information when the conditions at the implantation site or elsewhere in the body have changed.

SUMMARY

The present invention relates to devices, systems, and methods for delivering and positioning an implantable medical device (IMD) at desired location within a patient's body. The present invention also relates to devices, systems, and methods for evaluating an acoustic communication link between an IMD and a communicating device in acoustic communication with the IMD. A system for delivering and positioning an IMD in accordance with an illustrative embodiment includes a catheter adapted to deliver the IMD, and an implant assist device in wireless communication with the IMD via an acoustic communication link. The IMD can include a biosensor adapted to sense one or more physiologic parameters within the body, and at least one acoustic transducer configured to transmit and receive acoustic signals to and from the implant assist device. The implant assist device may comprise an external device or another implanted device, and includes at least one acoustic transducer adapted to receive the acoustic signal transmitted by the implantable device and to transmit an acoustic signal to the implantable device. The implant assist device includes control/processing circuitry that evaluates a performance of the acoustic link based on one or more parameters associated with the acoustic signals. In some embodiments, the implant assist device can be used by a clinician as an aid in deploying and positioning the IMD within the body. Once implanted, the implant assist device can also be used to periodically confirm the status of the acoustic communication link to ensure that the link is sufficient to continue to transmit sensor data and device status information to another device.

A method for delivering and positioning an IMD in accordance with an illustrative embodiment includes introducing a delivery catheter into a patient's body, the catheter including a distal portion having a lumen containing an IMD including a biosensor and an acoustic transducer adapted to transmit an acoustic signal; advancing the catheter to a target region within the patient's body; establishing an acoustic link between the IMD contained within the catheter and an implant assist device including an acoustic transducer adapted to receive the acoustic signal and control/processing circuitry for evaluating a signal strength and/or quality of the acoustic link; providing information to a user interface indicating the signal strength and/or quality of the acoustic link; and deploying the IMD within the patient's body.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
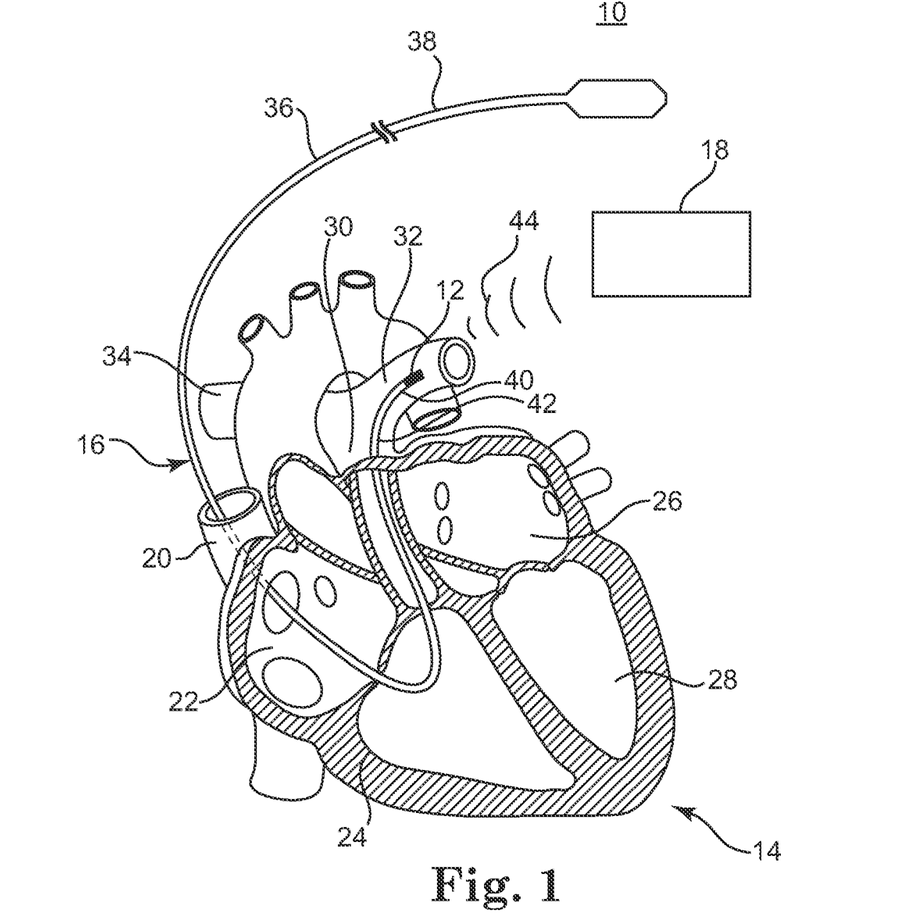
FIG. 1 is a schematic view of a system for delivering an implantable medical device at a target location within a patient's body according to an illustrative embodiment.

FIG. 1 is a schematic view of a system 10 for delivering and positioning an implantable medical device (IMD) 12 at a target location within a patient's body according to an illustrative embodiment. The system 10, illustratively a system for delivering and positioning an IMD 12 within a patient's heart 14 or into a vessel leading into or from the heart 14, includes a delivery catheter 16 adapted to transport the IMD 12 through the body. An implant assist device 18 is used to assist in the placement location and positioning of the IMD 12 within the body, and to confirm the adequacy of an acoustic communication link between the IMD 12 and the implant assist device 18 and/or another internal or external device in acoustic communication with the IMD 12 prior to or following implantation of the IMD 12 within the body. As shown in FIG. 1, the heart 14 includes a superior vena cava 20, a right atrium 22, a right ventricle 24, a left atrium 26, a left ventricle 28, and a main pulmonary artery 30 which leads to the left pulmonary artery 32 and the right pulmonary artery 34.

In the illustrated embodiment, the IMD 12 is configured to wirelessly communicate with the implant assist device 18 by transmitting a single acoustical pulse or series of acoustic pulses to the implant assist device 18 from a location within the interior of the delivery catheter 16. In the embodiment of FIG. 1, the implant assist device 18 is positioned at a location external to the patient's body. In some embodiments, for example, the implant assist device 18 may comprise an external communicating device which, in addition to aiding in the delivery and positioning of the IMD 12 within the body as discussed further herein, can be configured to receive sensor data and device status information from the IMD 12 when activated within the body. In other embodiments, the implant assist device 18 can comprise a device that is temporarily or permanently implanted within the patient's body, either as a stand-alone device or integrated as part of another implanted device such as a pacemaker and/or defibrillator. In some embodiments, the implant assist device 18 may also be used to program or alter the operation of the IMD 12.

The IMD 12 may comprise any type of chronically implanted device adapted to deliver therapy to the patient and/or to monitor various physiological parameters, properties, and functions within the body. For example, the IMD 12 can be used for sensing blood pressure, temperature, blood gas content, strain, fluid flow, chemical properties, electrical properties, magnetic properties, and other physiological properties. According to one embodiment, and as shown in FIG. 1, the IMD 12 can be configured to monitor blood pressure in a pulmonary artery 32. The IMD 12 can also be configured to sense, measure, calculate, or derive associated parameters such as, for example, flow rate, maximum and minimum pressure, the time rate of change (slope) of the pressure, and atmospheric pressure. In other embodiments, the IMD 12 can comprise a glucose level monitor, a pulmonary sound sensor, a satellite pacing device, or any other remote sensing or therapy-delivering device.

The delivery catheter 16 can be used to deliver and position the IMD 12 at a target region within the body that increases the signal strength and quality of the acoustic communications between the IMD 12 and the implant assist device 18, or between the IMD 12 and another internal or external device that communicates with the IMD 12. The delivery catheter 16 includes an elongate shaft 36 having a proximal portion 38, a distal portion 40, and an interior lumen 42 capable of retaining the IMD 12 therein during delivery.

As discussed further herein, the catheter 16 can be delivered to a target implantation region and repositioned as necessary or desired to obtain an optimal position for establishing an acoustic telemetry link between the IMD 12 and the implant assist device 18, or between the IMD 12 and another implant or external device that communicates with the IMD 12. If, for example, the implant assist device 18 is provided as part of an external monitor adapted to receive sensor data and device status information transmitted from the IMD 12, the catheter 16 can be delivered to a target implantation region and repositioned as necessary or desired to obtain an optimal position for receiving acoustic pulses transmitted by the IMD 12 and/or for transmitting acoustic pulses to the IMD 12. According to one embodiment, and as shown in FIG. 1, the catheter 16 can be used to deliver and position the IMD 12 in the left pulmonary artery 32. In other embodiments, the IMD 12 can be delivered and positioned in the main pulmonary artery 30, or in the right pulmonary artery 34. In still other embodiments, the IMD 12 can be delivered and positioned in other regions of the vasculature, in other body lumens, or in other areas of the body. Once positioned, the IMD 12 may be withdrawn from within the interior lumen 42 of the catheter 16 and deployed in the patient's body.

In some embodiments, the catheter 16 can be used to deliver and position the IMD 12 at an acceptable acoustic position within the target implantation region prior to being deployed within the body. An acceptable acoustic position within the target region may be defined generally as a position where the acoustic losses between the IMD 12 and a communicating device are minimized, and where the signal strength and quality of the acoustic communication is acceptable when compared against a predetermined or user-selected threshold value.

The implant assist device 18 can be used to assist in delivering and positioning the IMD 12 at an acceptable acoustic position within the target region of the patient's body. As shown in FIG. 1, the implant assist device 18 is configured to receive acoustic signals 44 transmitted by the IMD 12. Additionally, the implant assist device 18 is also configured to transmit acoustic signals to be received by the IMD 12 prior to deployment of the IMD 12 from within the delivery catheter 16 (e.g., during delivery of the IMD 12 within the body) or subsequent to deployment of the IMD 12 within the body. The implant assist device 18 converts the acoustic signal 44 received from the IMD 12 into an electrical signal, and using this signal as feedback, evaluates the strength and quality of the acoustic telemetry link. Based on this information, the clinician may adjust the position of the delivery catheter 16 containing the IMD 12 until an acceptable acoustic position has been identified. Once identified, the IMD 12 can then be removed from the interior lumen 42 of the delivery catheter 16 and deployed within the body.

During transmission of the acoustic signal 44 through the body, absorption and spreading of the acoustic energy within the body tissue results in the attenuation of the acoustic energy received by the implant assist device 18. The attenuation is mostly due to spreading losses resulting from the acoustic energy dispensing within the body volume as well as absorption losses in the intrabody medium and reflection losses at the boundaries of the intrabody medium such as at the interface between different tissue types (e.g., between soft tissue and bone) where there may be an abrupt change in acoustic impedance. The amount of attenuation loss occurring within the body is dependent on several factors, including the physical anatomy between the IMD 12 and the implant assist device 18, the frequency of the acoustic transmission, as well as other factors. As a result of the acoustic losses and reflections occurring in the intrabody medium and at the medium interface, the magnitude and duration of the acoustic energy received by the implant assist device 18 from the IMD 12 may be significantly altered from that originally emitted by the IMD 12.

Figure 2:
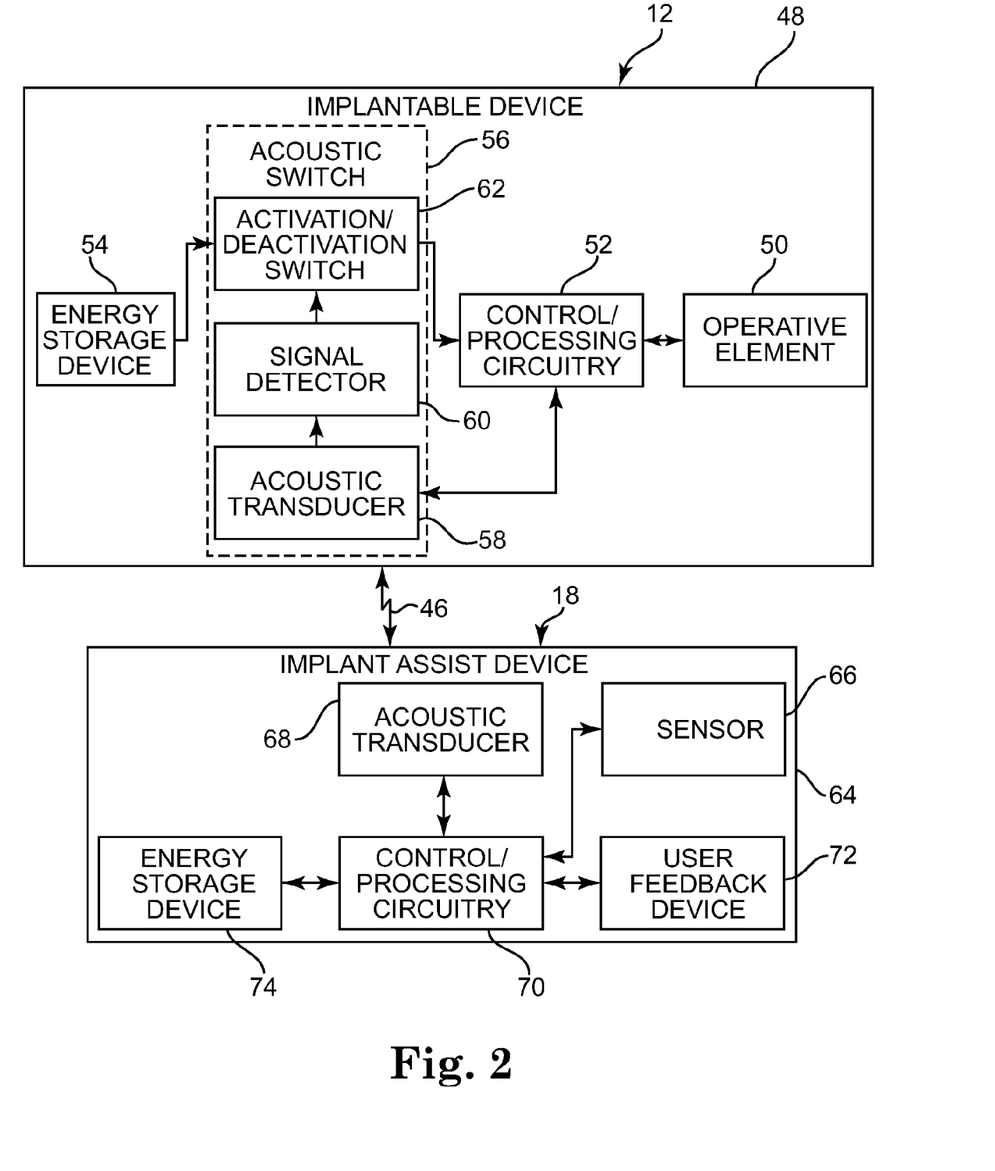
FIG. 2 is a schematic view of the implantable medical device and implant assist device of FIG. 1 according to an illustrative embodiment.

FIG. 2 is a schematic view of the IMD 12 and the implant assist device 18 of FIG. 1 according to an illustrative embodiment. The IMD 12 is configured for acquiring physiological information from a patient and/or providing therapy to the patient. The implant assist device 18 is configured for interacting with the IMD 12 via an acoustic telemetry link 46. For example, the implant assist device 18 may wirelessly receive an acoustic signal from the IMD 12 and/or may wirelessly transmit an acoustic signal to the IMD 12. In some embodiments, another implantable medical device may wirelessly interact with the IMD 12, either directly or indirectly via the implant assist device 18 in a manner described, for example, in U.S. patent application Ser. No. 11/373,005, entitled "Body Attachable Unit In Wireless Communication With Implantable Devices," which is expressly incorporated herein by reference in its entirety for all purposes. In some embodiments, the IMD 12 and/or the implant assist device 18 may wirelessly interact with an external auxiliary device such as an external computer and/or a caregiver server or database.

The IMD 12 can be selectively actuated between an active state, during which the IMD 12 expends energy to perform one or more functions within the body, and a standby state, during which the IMD 12 is not currently performing its intended medical function and most or all of the energy-consuming circuitry is powered off. The IMD 12 can be configured to remain in the standby state until awoken to the active state by the implant assist device 18. In some embodiments, the implant assist device 18 is capable of transmitting an activation or wake-up command to activate the IMD 12. The implant assist device 18 can also be configured to transmit a sleep command that deactivates the IMD 12. In some embodiments, the IMD 12 may automatically deactivate after a certain period of time has elapsed or after a particular medical function has been performed.

The implant assist device 18 wirelessly communicates with the IMD 12 using acoustic energy (e.g., at a relatively low frequency of 40 kHz), and in particular, by transmitting and receiving acoustic energy through the body. In some embodiments, the implant assist device 18 may wirelessly receive the acoustic energy from the IMD 12 and/or may transmit acoustic energy to control or operate the IMD 12. In some embodiments, the implant assist device 18 may also transmit acoustic energy for charging the IMD 12.

In some embodiments, the implant assist device 18 is an external device that can be acoustically coupled to the patient's body. In certain embodiments, for example, the implant assist device 18 is a portable, battery operated device that can be held in contact with the patient's body by a clinician or the patient. In other embodiments, the implant assist device 18 is attached to the patient's body using an attachment mechanism such as a strap, patch, belt, or any other means for coupling the device 18 to the patient's body. Further details regarding various means of securely attaching control devices to patients are provided in U.S. Pat. No. 7,283,874, entitled "Acoustically Powered Implantable Stimulating Device," which is expressly incorporated herein by reference in its entirety for all purposes. In some embodiments, the implant assist device 18 can also be a part of another external device (e.g. an external monitor, a computer, a patient monitoring system, etc.).

In an alternative embodiment, the implant assist device 18 is configured to be temporarily implanted at a location within the patient's body. For example, in those embodiments where the IMD 12 is configured to acoustically communicate with an implant such as a pacemaker or defibrillator, the implant assist device 18 may be temporarily placed in or near the body cavity that normally supports the implant. Such placement of the implant assist device 18 ensures that the acoustic signal transmitted by the IMD 12 and received by the device 18 follows a path similar to that followed once the IMD 12 is implanted within the body and is placed into communication with the implant. In some embodiments, the implant assist device 18 may be integrated into another implant such as a pacemaker or defibrillator.

The structure of the IMD 12 will now be described. In the illustrative embodiment of FIG. 2, the IMD 12 includes a casing 48, an operative element 50, control/processing circuitry 52, an energy storage device 54, and an acoustic switch 56, which includes an acoustic transducer 58, a signal detector 60 and a deactivation/activation switch component 62. In some embodiments, the acoustic transducer 58 is configured to both transmit and receive acoustic signals. In other embodiments, the IMD 12 includes at least one acoustic transducer configured to transmit an acoustic signal and at least one acoustic transducer configured to receive an acoustic signal.

The casing 48 houses all of the internal components of the IMD 12, is composed of a suitable biocompatible material, and is hermetically sealed to isolate the components from the environment outside of the IMD 12. Further details regarding the construction of casings for implantable devices is described, for example, in U.S. Pat. No. 6,764,446, entitled "Implantable Pressure Sensors And Methods For Making And Using Them," which is expressly incorporated herein by reference in its entirety for all purposes.

The operative element 50 may comprise a biosensor that generates a signal related to a sensed physiological parameter. Such physiological parameters may include, but are not limited to, pressure, temperature, electrical impedance, position, strain, pH, blood flow, radiation level, glucose level, and the like. Additional sensors may be provided for the measurement of other physiological parameters and/or for calibrating the IMD 12, if desired. The operative element 50 may also comprise a bioactuator that provides therapy to the patient. In certain embodiments, for example, the bioactuator may be used for providing drug delivery, neurostimulation therapy, cardiac pacing therapy, or defibrillation therapy to the patient. Additional operative elements may also be provided for performing other functions within the body.

The control/processing circuitry 52 includes circuitry for activating and/or controlling the operative element 50. For example, if the operative element 50 is a biosensor, the control/processing circuitry 52 can be used to process one or more physiological parameters sensed by the operative element 50, and wirelessly transmit such physiological information via the acoustic transducer 58 to another implanted device and/or external monitor. If the operative element 50 is a bioactuator, the control/processing circuitry 52 can be used to control the operative element 50 for providing therapy to the patient using a pre-programmed protocol.

The control/processing circuitry 52 may also include memory for storing information such as data received from the operative element 50 and/or commands for use internally. The control/processing circuitry 52 may include an oscillator or other circuitry for modulating the acoustic signals transmitted to the implant assist device 18, and for measuring time. In some embodiments, the control/processing circuitry 52 may include a processor for analyzing, interpreting, and/or processing the signals received by the operative element 50 and the signals received from the implant assist device 18.

The energy storage device 54 may be any of a variety of known devices such as a battery or a power capacitor. In some embodiments, the energy storage device 54 includes both a capacitor and a primary, non-rechargeable battery. The energy storage device 54 may be capable of storing electrical energy substantially indefinitely unless actively discharged. In addition, the energy storage device 54 may be capable of being charged from an external source, and in particular, from acoustic energy transmitted to the IMD 12 from the implant assist device 18 or another device in acoustic communication with the IMD 12.

In certain embodiments, the acoustic transducer 58 includes one or more piezoelectric transducer elements configured for transmitting and receiving acoustic signals. In a reception mode of operation, the acoustic transducer 58 generates an electrical signal proportional to the magnitude of the acoustic signal wirelessly received from the implant assist device 18, which is then conveyed to the control/processing circuitry 52 when the IMD 12 is in the active state. Similarly, in a transmission mode of operation the acoustic transducer 58 generates an acoustic signal proportional to the magnitude of the electrical signal conveyed from the control/processing circuitry 52 when the IMD 12 is in the active state, which is then wirelessly transmitted to the implant assist device 18.

The signal detector 60 is configured to generate an activation trigger signal to activate the IMD 12 via the deactivation/activation switch component 62. The activation trigger signal is generated by the signal detector 60 when the electrical signal generated by the acoustic transducer 58 exceeds a specific voltage threshold. The deactivation/activation switch component 62 is the component through which current is delivered from the energy storage device 54 to the control/processing circuitry 52 when actuated. In response to the generation of the activation trigger signal by the signal detector 60, the switch component 62 is actuated to allow current to flow to the control/processing circuitry 52, thereby placing the IMD 12 in the active state. The switch component 62 can also be actuated to prevent current from flowing to the control/processing circuitry 52, thereby placing the IMD 12 in the standby state. Further details regarding the general construction and function of acoustic switches are disclosed in U.S. Pat. No. 6,628,989, entitled "Acoustic Switch And Apparatus And Methods For Using Acoustic Switches Within The Body," which is expressly incorporated herein by reference in its entirety for all purposes.

An acoustic activation or wake-up command can be used to activate the IMD 12 when the IMD 12 is in the standby state. When in the standby state, the electrical signal is not passed to the control/processing circuitry 52, but rather acts solely to close the acoustic switch 56. To activate the IMD 12, one or more activation acoustic energy pulses can be transmitted from the implant assist device 18 to the IMD 12, which can be received by the acoustic transducer 58. Upon excitation, the acoustic transducer 58 generates an electrical signal that causes the signal detector 60 to generate a trigger signal that is used to close, open, or otherwise activate the switch component 62.

The structure of the implant assist device 18 will now be described. In the illustrative embodiment of FIG. 2, the implant assist device 18 includes a casing 64, an on-board sensor 66, an acoustic transducer 68, control/processing circuitry 70, an audio/visual user feedback device 72, and an energy storage device 74. The casing 64 is configured to house the components of the implant assist device 18, and in some embodiments is sized and shaped to be comfortably held or worn by the patient or the clinician. Alternatively, in those embodiments in which the implant assist device 18 is configured to be implanted within the body, the casing 64 may comprise a suitable biocompatible material.

The sensor 66 may comprise a biosensor that generates a signal in response to a measured parameter. In one embodiment, for example, the sensor 66 may comprise a barometric pressure sensor configured to measure barometric pressure for use by the IMD 12. The implant assist device 18 may include one or more additional sensors such as an ECG electrode sensor, an impedance sensor, a systemic blood pressure sensor, a posture sensor, a global positioning system (GPS) sensor, an activity sensor, a temperature sensor, and/or an oximeter.

The acoustic transducer 68 for the implant assist device 18 is configured to both transmit and receive acoustic signals to and from the IMD 12. In other embodiments, the implant assist device 18 includes at least one transducer configured for receiving an acoustic signal from the IMD 12 and at least one transducer for transmitting an acoustic signal to the IMD 12. In a reception mode, the acoustic transducer 68 generates an electrical signal proportional to the magnitude of acoustic energy received by the transducer 68, which is then conveyed to the control/processing circuitry 70. In similar fashion, in a transmission mode the acoustic transducer 68 generates an acoustic signal proportional to the magnitude of the electrical energy generated by the control/processing circuitry 70. An example acoustic transducer that can be used in small profile external units is disclosed in U.S. patent application Ser. No. 11/287,557, entitled "Implantable Medical Device with Integrated Acoustic Transducer," which is expressly incorporated herein by reference in its entirety for all purposes.

The control/processing circuitry 70 includes circuitry for activating or controlling the sensor 66 and for receiving signals from the sensor 66. In some embodiments, the control/processing circuitry 70 may include an oscillator or other circuitry for modulating the acoustic signals transmitted to the IMD 12 via the acoustic transducer 68, and for measuring time. In some embodiments, the control/processing circuitry 70 can also include signal detection circuitry for detecting acoustic signals received from the IMD 12 via the acoustic transducer 68 or from another acoustic transducer coupled to the implant assist device 18.

In some embodiments, the control/processing circuitry 70 includes a processor for analyzing, interpreting, and/or processing the received acoustic signals, and a memory for storing the processed information and/or commands for use internally. In certain embodiments, for example, the control/processing circuitry 70 can be used to analyze the strength and quality of the acoustic signal received from the IMD 12.

The control/processing circuitry 70 can also be used to analyze other characteristics of the acoustic signals received from the IMD 12 and/or other information received from the IMD 12. The control/processing circuitry 70 can also determine one or more parameters to change in the IMD 12. The control/processing circuitry 70 can be configured as a digital signal processor (DSP), a field programmable gate array (FPGA), an application specific integrated circuit (ASIC)-compatible device, and/or any other hardware components or software modules for processing, analyzing, storing data, and controlling the operation of the implant assist device 18.

The user feedback device 72 can include a screen or display panel for communicating information to the clinician and/or to the patient. For example, the screen or display panel can display visual information indicative of the strength and/or quality of the acoustic signal received from the IMD 12 for use in assessing whether a target region within the body is acceptable for providing an adequate acoustic link between the IMD 12 and the implant assist device 18 and/or between the IMD 12 and another implant or external device that acoustically communicates with the IMD 12. In certain embodiments, where the implant assist device 18 is integrated into another device, the screen or display panel may also be used to display other information such as any physiological parameters monitored by the IMD 12. The implant assist device 18 may also provide aural and tactile feedback to the clinician and/or patient.

In some embodiments, the implant assist device 18 includes an interface for connecting to the Internet, to a cell phone, and/or to other wired or wireless means for downloading or uploading information and programs, debugging data, and upgrades. In some embodiments, this connection may also be used for charging the energy storage device 74 within the implant assist device 18. According to some embodiments, the implant assist device 18 is also capable of operating in two modes: a user mode that provides useful clinical information to the patient or a caregiver, and a diagnostic mode that provides information to an individual for calibrating and/or servicing the implant assist device 18.

Figure 3A:
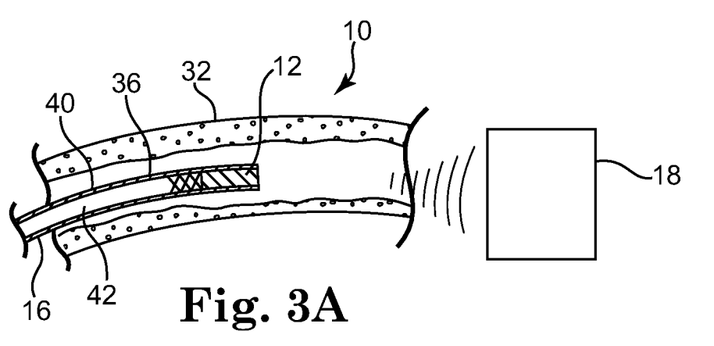
FIGS. 3A-3C are several schematic views showing a system used to deliver and position an IMD at a target location within a patient's body according to an illustrative embodiment.
Figure 3B:
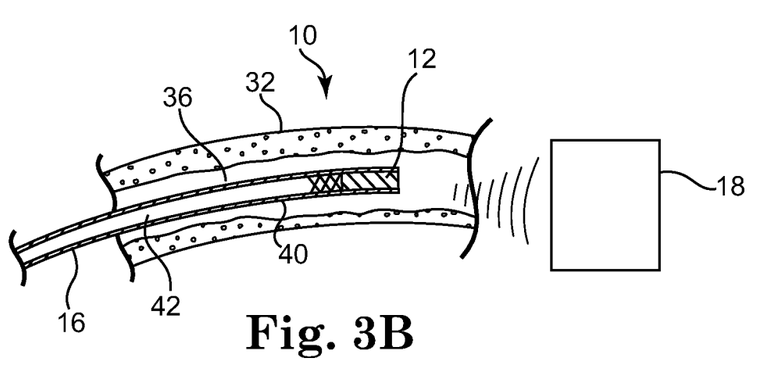
Figure 3C:
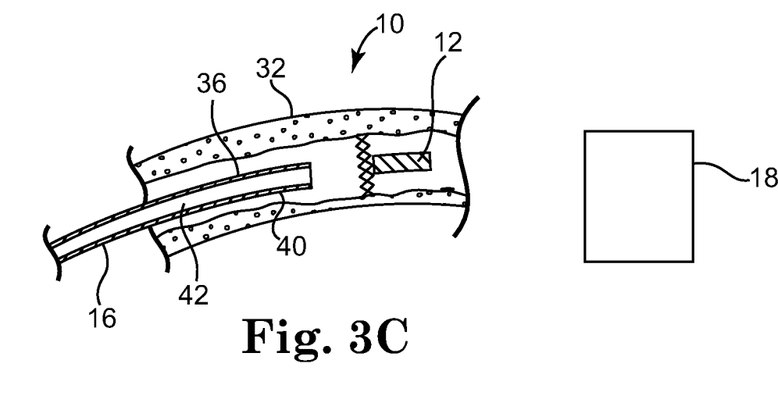

FIGS. 3A-3C are several schematic views showing a system 10 used to deliver and position an IMD 12 at a target region within a patient's body. In a first view shown in FIG. 3A, the IMD 12 is initially disposed within the interior lumen 42 of the delivery catheter 16. The catheter 16 containing the IMD 12 can be delivered to a target region within the body using delivery techniques known to those of skill in the art and under visualization (e.g. via fluoroscopy). According to one embodiment, and as shown in FIGS. 3A-3C, the delivery catheter 16 is used to deliver the IMD 12 to a target region within a pulmonary artery 32.

In some embodiments, the implant assist device 18 is acoustically coupled to the patient's skin at a location adjacent to the target region of the body where implantation of the IMD 12 is desired, and where communication between the IMD 12 and an external communicating device (e.g., an external monitor) is likely. In other embodiments, the implant assist device 18 may be temporarily implanted within the patient's body at a location at or near where another implant that acoustically communicates with the IMD 12 is situated. In some embodiments, for example, the implant assist device 18 can be placed in or near the pocket within the body that contains an implanted pulse generator that acoustically communicates with the IMD 12.

To assess whether acoustic communication between the IMD 12 and the implant assist device 18 or another implant or external device is adequate, the implant assist device 18 can be configured to transmit an acoustic signal to the IMD 12 prior to deployment. Upon receiving the acoustic signal, the IMD 12 enters into a transmission mode of operation and transmits an acoustic signal back to the implant assist device 18. In some embodiments, the IMD 12 transmits an acoustic signal to the implant assist device 18 while the IMD 12 is partially or entirely disposed within the interior lumen 42 of the catheter 16. The implant assist device 18 evaluates the strength and quality of the acoustic signal received from the IMD 12 and then provides this information to the clinician via the user feedback device 72 as discussed, for example, with respect to FIG. 2.

The displayed information can then be used by the clinician to adjust the positioning of the IMD 12 within the target region of the patient's body by moving the delivery catheter 16 in either a proximal or a distal direction within the artery 32 and/or by rotating the catheter 16 within the artery 32. As can be further seen in a second view in FIG. 3B, for example, the position of the IMD 12 within the artery 32 has been adjusted by advancing the delivery catheter 16 in a distal direction within the artery 32. The process of verifying the acoustic performance at each new position within the target implantation region is then repeated, as described with reference to FIG. 3A, in order to verify the strength and/or quality of the acoustic transmission at each location.

Once an acceptable acoustic position within the target implantation region has been identified, the IMD 12 can then be deployed and the delivery catheter 16 withdrawn from the patient's body. FIG. 3C shows the IMD 12 deployed within the pulmonary artery 32. Once the IMD 12 is implanted within the body, the implant assist device 18 can also be used to verify the signal strength and quality of the acoustic transmission from the implanted IMD 12, if desired. In some embodiments, for example, the IMD 12 may transmit an acoustic signal to the implant assist device 18 from a position outside of the catheter 16 once the IMD 12 has been withdrawn from the interior lumen 42. If the strength and/or quality of the acoustic transmission is poor or unacceptable after implantation, the IMD 12 can be retrieved and re-deployed as necessary before fibrous in-growth at the site of implantation has occurred. Once implanted, the IMD 12 can then be activated to perform its designated function. Subsequent to implantation of the IMD 12, the implant assist device 18 can also be utilized to periodically evaluate the acoustic communication link to determine whether the IMD 12 can continue to accurately transmit sensor data and device status information in view of any physiological changes that may have occurred within the body over time.

Figure 4:
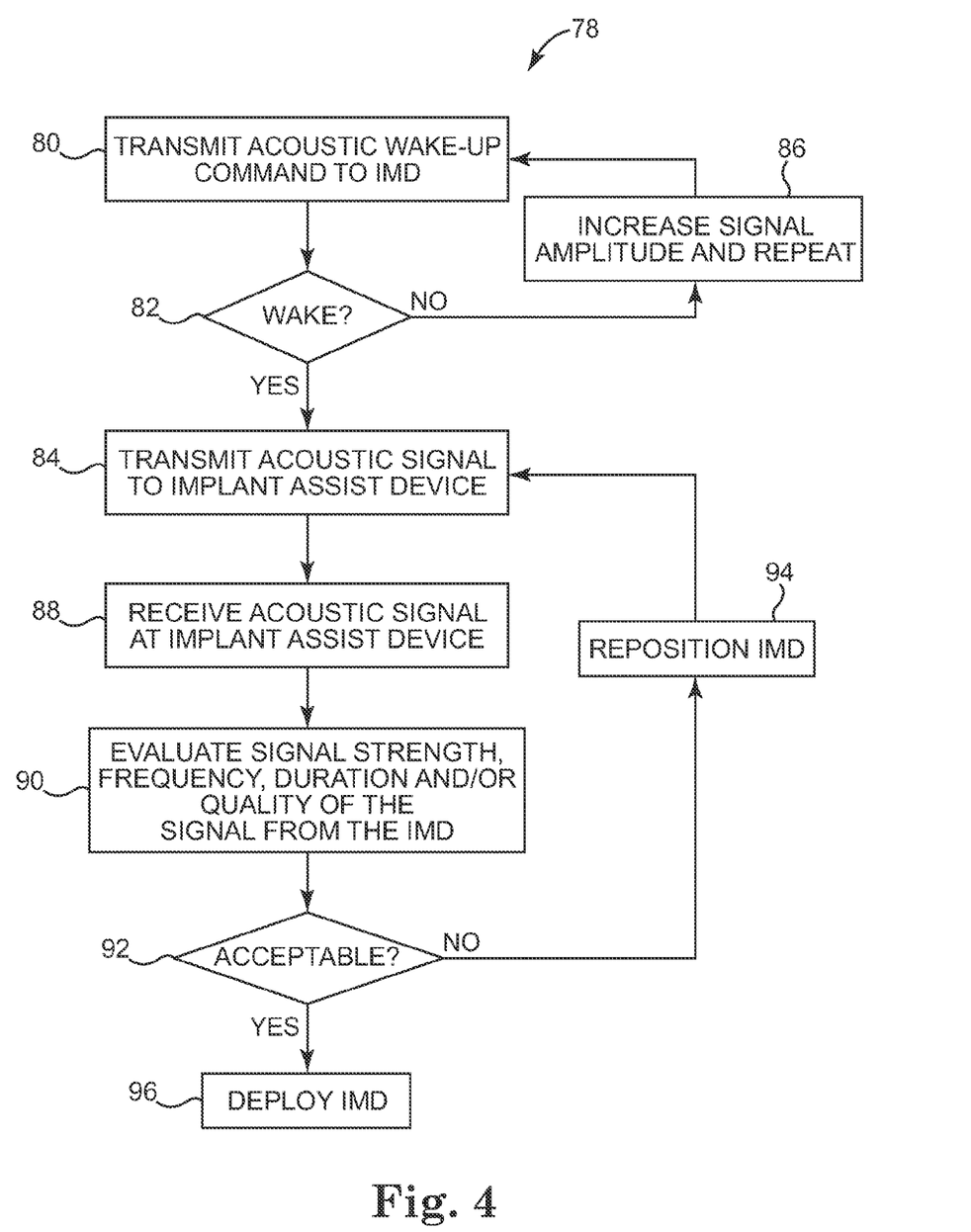
FIG. 4 is a flow diagram of a method for evaluating an acoustic communication link between an IMD and an implant assist device according to an illustrative embodiment.

FIG. 4 is a flow diagram of an illustrative method 78 for evaluating an acoustic communication link between an IMD 12 and an implant assist device 18. The method 78 may represent, for example, several steps used in delivering and positioning an IMD 12 at a target region within a patient's body using the implant assist device 18 as an aid to evaluate communication performance. In one embodiment, as shown in FIG. 4, the implant assist device 18 may initially send an acoustic wake-up command to an IMD 12 located within a delivery catheter 16 prior to implantation of the IMD 12 in order to transition the IMD 12 from a stand-by mode or sleep mode of operation to an active mode of operation (block 80). If the initial command is of a sufficient amplitude to wake up the IMD 12 (block 82), the IMD 12 responds by transmitting an acoustic signal back to the implant assist device 18 (block 84). If no response is received from the IMD 12, or if the amplitude of the acoustic signal received from the IMD 12 is too low or the timing is inappropriate, another acoustic wake-up command can be transmitted by the implant assist device 18 to the IMD 12.

With each subsequent transmission from the implant assist device 18, the amplitude of the wake-up command can be increased (block 86). Other parameters such as the frequency and/or duration of the wake-up command can also be adjusted. This process is repeated until the IMD 12 reaches an activated state.

In an activated state, the IMD 12 transmits an acoustic signal (block 84). The implant assist device 18 receives the acoustic signal transmitted by the IMD 12 (block 88) and converts this signal into an electrical signal that is fed to the control/processing circuitry 70. The control/processing circuitry 70 then evaluates the signal strength, frequency, duration, and/or quality of the acoustic signal received from the IMD 12 to ascertain the performance of the acoustic link between the IMD 12 and the implant assist device 18 (block 90). In some embodiments, for example, the implant assist device 18 is configured to compare the signal strength of the acoustic signal against a predetermined set of signal criteria based on the implantation location to determine if the implantation location is acceptable. For implantation in a pulmonary artery, for example, the IMD 12 can be configured to transmit an acoustic signal having a predetermined amplitude to the implant assist device 18 in order to determine whether implantation of the IMD 12 at that location is appropriate, or if repositioning of the IMD 12 is necessary.

This information is then provided to the clinician via the user feedback device 72 to ascertain whether the signal strength and quality of the acoustic link is acceptable (block 92). According to one exemplary embodiment, the information displayed by the implant assist device 18 can include a number of bars indicating the signal strength and quality of the acoustic signal transmitted by the IMD 12. In some embodiments, the bars can be both red and green to permit the clinician to quickly determine whether the implantation location is acceptable. When the strength and quality of the acoustic signal received reaches an acceptable level, for example, the screen or display panel may display a number of bars that are all green indicating that the communication link is adequate. According to another embodiment, for example, the user feedback device 72 may simply display a symbol (e.g., a green light) when the strength and quality of the acoustic signal transmitted by the IMD 12 has reached an acceptable performance level. Other means of providing visual, aural, and/or tactile feedback to the clinician are also possible.

With each subsequent adjustment of the IMD 12 within the patient's body (block 94), the process is repeated until the implant assist device 18 indicates that the strength and quality of the acoustic link has reached an acceptable level. An acceptable level of performance may be, for example, a signal to noise (S/N) ratio equal to or greater than about 2. Other parameters may also be used by the implant assist device 18 to assess the performance of the acoustic link including, for example, noise floor level, carrier frequency, signal timing, signal duration, and/or signal morphology. Other parameters such as that discussed further herein with respect to FIG. 5 may also be used by the implant assist device 18, or in some cases also the IMD 12, to assess the performance of the acoustic link. When the signal strength and quality of the received acoustic signal is deemed acceptable, the IMD 12 may then be deployed (block 96).

In some embodiments, a wake-up threshold margin associated with the IMD 12 may be used to assess the signal strength and quality of the acoustic link. The wake-up threshold margin may represent, for example, the additional signal strength transmission capability of the implant assist device 18 as compared to a wake-up threshold level required to wake-up the IMD 12 from a standby state to an active state. For example, if an implant assist device 18 is capable of transmitting an acoustic signal at a level of between 1 and 10, and the wake-up threshold for the IMD 12 is 2, the wake-up threshold margin is therefore 8 (i.e., 80%), which may indicate an adequate acoustic communication link between the IMD 12 and the implant assist device 18. As another example, if the implant assist device 18 is capable of transmitting a signal level of between 1 and 10, and the wake-up threshold for the IMD 12 is 9, the wake-up threshold margin is 1 (i.e., 10%), which may indicate an inadequate acoustic communication link between the IMD 12 and the implant assist device 18.

According to some embodiments, the implant assist device 18 can also be used to ascertain the performance of the acoustic communication link after implantation, following the steps as described above. In some cases, for example, the implant assist device 18 can be used by a clinician as an aid to periodically check the status of the communication link subsequent to implantation of the IMD 12 within the body to determine whether any physiological changes at the implantation site or elsewhere in the body are affecting the acoustic communication link. The implant assist device 18 may also be used as an aid to verify that the IMD 12 itself is operating properly.

Figure 5:
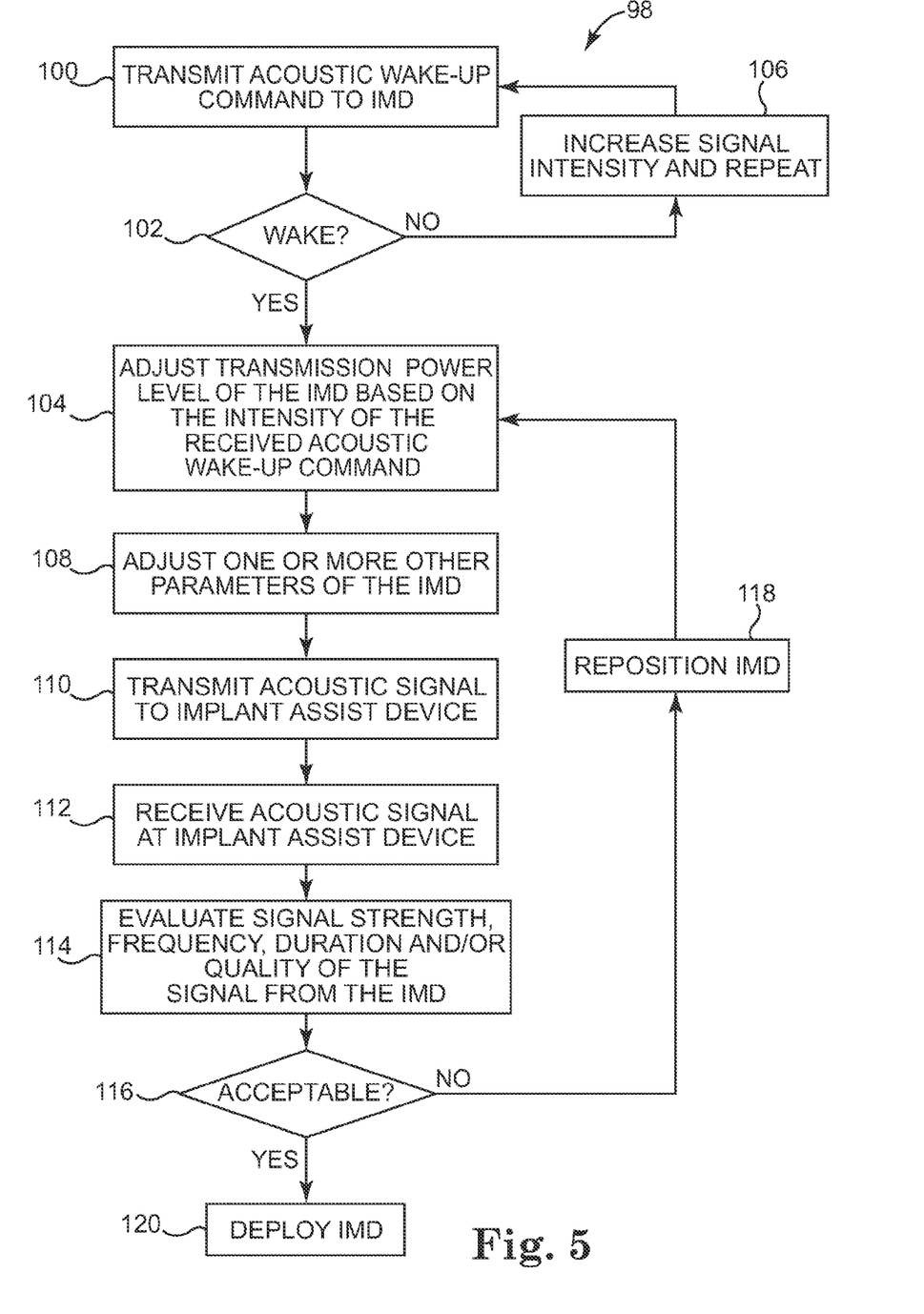
FIG. 5 is a flow diagram of a method for evaluating an acoustic communication link between an IMD and an implant assist device according to another illustrative embodiment.

FIG. 5 is a flow diagram of another illustrative method 98 for evaluating acoustic communication link between an IMD 12 and an implant assist device 18. Similar to the method 78 described above with respect to FIG. 4, the method 98 may represent, for example, several steps used in delivering and positioning an IMD 12 at a target region within a patient's body using the implant assist device 18 as an aid to evaluate communication performance. As shown in FIG. 5, the implant assist device 18 may initially send an acoustic wake-up command to an IMD 12 located within a delivery catheter 16 prior to implantation of the IMD 12 in order to transition the IMD 12 from a stand-by or sleep mode of operation to an active mode of operation (block 100). Initially, the IMD 12 is programmed to wake up and transition to the active mode of operation in response to an acoustic wake-up command having a pre-determined amplitude level. In some embodiments, for example, the IMD 12 is initially programmed to transition to the active mode of operation in response to an acoustic wake-up command transmitted by the implant assist device 18 at a reduced power level such as, for example, a 50% transmission power level. If the initial, reduced-power wake-up command is of a sufficient amplitude to wake up the IMD 12 (block 102), the control/processing circuitry 52 within the IMD 12 adjusts the transmission power level of the IMD 12 to match the power level of the received acoustic wake-up command (block 104) and then transmits an acoustic signal at the adjusted power level back to the implant assist device 18 (block 106). If, for example, the acoustic wake-up command received by the IMD 12 has a 50% transmission power level and is sufficient to wake up the IMD 12, the control/processing circuitry 52 within the IMD 12 can adjust the transmission power level of the IMD 12 to 50% and then transmit an acoustic signal at the 50% power level back to the implant assist device 18.

If no response is received back from the IMD 12, or if the amplitude of the acoustic signal received from the IMD 12 is too low, the implant assist device 18 may increase power level to a new level (block 106) and transmit another acoustic wake-up command to the IMD 12 (block 100). If, for example, the previous acoustic wake-up command was set at a 50% power level, and the implant assist device 18 did not receive a response back from the IMD 12, the implant assist device 18 may increase the power level to a new level (e.g., 60%), and then transmit another acoustic wake-up command at this new level. With each subsequent transmission from the implant assist device 18, the amplitude of the wake-up command can be increased (block 106). The process is then repeated until the IMD 12 reaches an activated state.

The implant assist device 18 can be configured to vary one or more other parameters of the acoustic wake-up signal transmitted to the IMD 12 in addition to or in lieu of the transmission power level (block 108). In some embodiments, for example, the implant assist device 18 may vary the pulse count or pulse duration of the acoustic wake-up command transmitted to the IMD 12 to determine a minimum pulse count or duration necessary to wake up the IMD 12 at a particular amplitude level. The carrier frequency of the carrier signal provided as part of the acoustic wake-up command can also be adjusted to determine the frequency or range of frequencies that cause the IMD 12 to wake up at a particular amplitude level. The carrier frequency can be adjusted, for example, by sweeping the carrier signal across a range of frequencies, or by step-wise adjusting the frequency at discrete frequency levels. In some cases, this may permit the implant assist device 18 to determine a communication frequency that closely matches the resonance frequency of the acoustic transducer 58 of the IMD 12.

In an activated state, and in some embodiments, the implant assist device 18 may further download additional information to the IMD 12 that can be used to adjust the operation of the IMD 12 for purposes of evaluating the performance of the acoustic communication link. In some embodiments, for example, the implant assist device 18 may transmit a command to the IMD 12 causing the IMD 12 to adjust the receiver threshold and gain associated with the acoustic transducer 58, or to adjust the decode ratio (e.g., times out of 8) necessary to decode encoded sensor data sent by the IMD 12. The implant assist device 18 may also send other commands to the IMD 12 prompting the IMD 12 to adjust various communication parameters relating to the acoustic transmission from the IMD 12 to the implant assist device 18. Example parameters relating to the acoustic transmission from the IMD 12 to the implant assist device 18 may include the pulse count (e.g., the number of pulses per transmission) and the data rate (e.g., the time or duration between bits). The implant assist device 18 may also transmit a command that adjusts the clock frequency of the IMD 12 during uplink transmissions to the implant assist device 18.

The IMD 12 next transmits an acoustic signal (block 110). The implant assist device 18 receives the acoustic signal transmitted by the IMD 12 (block 112) and converts this signal into an electrical signal that is fed to the control/processing circuitry 70. The control/processing circuitry then evaluates the signal strength, frequency, duration, and/or quality of the acoustic signal received from the IMD 12 to evaluate the performance of the acoustic link between the IMD 12 and the implant assist device 18 (block 114). In some embodiments, for example, the implant assist device 18 may measure parameters such as the peak signal amplitude of the acoustic signal and the difference between the peak signal amplitude and a predetermined threshold based on the implantation location. The implant assist device 18 may also measure other parameters such as the pulse count of the received acoustic signal, the clock skew associated with the IMD 12, the bit error rate, and the bit correction rate. Other information such as the receiver gain and threshold of the implant assist device 18 and the blanking interval may also be determined. This information may then be provided to the clinician via the user feedback device 72 to ascertain whether the signal strength and quality of the acoustic link is acceptable (block 116). In some cases, a weighted sum that weighs multiple parameters (e.g., pulse count, clock skew, S/N ratio) together may be used to ascertain whether the signal strength and quality of the acoustic link is acceptable.

With each subsequent adjustment of the position of the IMD 12 within the patient's body (block 118), the process is then repeated until the implant assist device 18 indicates that the strength and quality of the acoustic link has reached an acceptable level. The IMD 12 may then be deployed (block 120) within the body. Subsequent to implantation, the implant assist device 18 can then be further used to periodically check the status of the communication link and/or the operation of the IMD 12.

Figure 6:
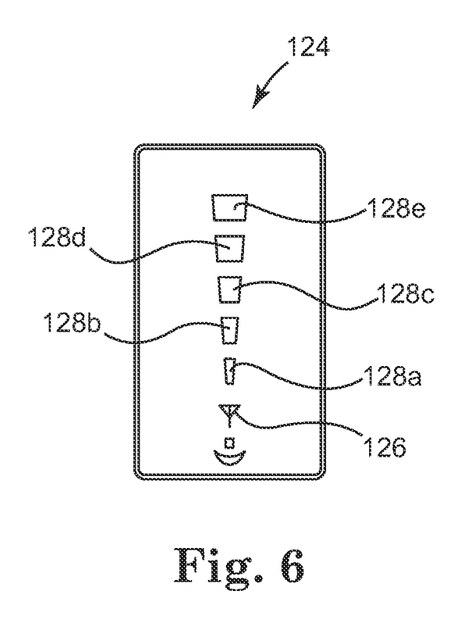
FIG. 6 is a schematic view showing an illustrative display panel that can be used to provide a clinician with feedback on the status of an acoustic communication link between an IMD and an implant assist device.

FIG. 6 is a schematic view showing an illustrative screen or display panel 124 that can be used to provide a clinician with feedback on the status of an acoustic communication link established between an IMD 12 and the implant assist device 18. In some embodiments, for example, the screen or display panel 124 may be provided as part of the user feedback device 72 described above with respect to FIG. 2 to provide a clinician with feedback on the status of an acoustic communication link between the IMD 12 and the implant assist device 18, or alternatively, between the IMD 12 and another internal or external device in acoustic communication with the IMD 12.

In the embodiment shown, the screen or display panel 124 includes a communication status icon 126 that indicates whether the implant assist device 18 is currently communicating with the IMD 12. Display of the communication status icon 126 on the screen or display panel 124 may indicate, for example, that the implant assist device 18 has transmitted an acoustic wake-up command to the IMD 12 and has successfully received an acoustic signal back from the IMD 12. A blinking communication status icon 126 may represent that the implant assist device 18 has transmitted an acoustic wake-up command to the IMD 12 and is awaiting a response back from the IMD 12. Other information regarding the status of the communication link, the operation of the IMD 12, and/or the operation of the implant assist device 18 may also be provided on the screen or display panel 124.

A number of signal strength bars 128a-128e on the screen or display panel 124 may provide the clinician with visual feedback of the signal strength and quality of the acoustic communication link established between the IMD 12 and the implant assist device 18. A greater number of bars 128a-128e on the display panel 124 may indicate a greater signal strength and/or quality whereas a fewer number of bars 128a-128e may indicate a diminished signal strength and/or quality. For example, as shown in FIG. 6, the illumination of two signal strength bars 128a,128b on the screen or display panel 124 may indicate that the acoustic communication link is sufficient but not optimal. As discussed previously with respect to FIGS. 4-5, this information may then be used by the clinician to determine whether to deploy the IMD 12 at a particular location or position within the body or, once the IMD 12 has been deployed, to determine whether the IMD 12 can continue to accurately transmit sensor data and device status information in view of any physiological changes that may have occurred within the body over time.

In some embodiments, the number of bars 128a-128e displayed may correspond to a weighted sum that utilizes multiple parameters associated with the performance of the acoustic communication link. By way of example and not limitation, the display of all five bars 128a-128e may represent that the IMD 12 is communicating at a 25% pulse count, a 4% clock skew, and a S/N ratio of 10. Display of four bars 128a-128d may represent, for example, that the IMD 12 is communicating at a 50% pulse count, a 3% clock skew, and a S/N ratio of 5. Display of three bars 128a-128c may represent, for example, that the IMD 12 is communicating at a 75% pulse count, a 2% clock skew, and a S/N ratio of 3. Display of two bars 128a-128b may represent, for example, that the IMD 12 is communicating at a 100% pulse count, a 1% clock skew, and a S/N ratio of 2. A single bar 128a may represent that the IMD 12 is communicating at its maximum settings (e.g., maximum signal amplitude, pulse count, etc.) and requires parity/CRC error correction. No bars on the screen or display panel 124 may represent that the implant assist device 18 received no response from the IMD 12 or that unrecoverable parity/CRC errors exist when the IMD 12 is communicating at its maximum settings. Other parameters may also be associated with each of the signal strength bars 128a-128e.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. An implant assist device for evaluating an acoustic communication link with an implantable device, the implantable device configured to transmit an acoustic signal at a location within a patient's body, the implant assist device comprising:
    at least one acoustic transducer adapted to receive the acoustic signal transmitted by the implantable device;
    circuitry configured to evaluate a performance of the acoustic communication link based at least in part on comparing a weighted sum of plurality of parameters of the acoustic signal transmitted by the implantable device against a predetermined set of signal criteria; and
    a user interface configured to provide information indicative of the performance of the acoustic communication link to a user, the user interface including a panel configured for providing feedback on a signal status and quality of the acoustic communication link for determining whether an implantation location is acceptable.

2. The implant assist device of claim 1, wherein the implant assist device is an external device.

3. The implant assist device of claim 1, wherein at least a portion of the implant assist device is an implantable device.

4. The implant assist device of claim 3, wherein the portion of the implant assist device that is an implantable device further comprises at least one acoustic transducer adapted to receive the acoustic signal transmitted by the implantable device.

5. The implant assist device of claim 4, wherein the portion of the implant assist device that is an implantable device further comprises circuitry configured to evaluate a performance of the acoustic communication link based at least in part on evaluating one or more parameters of the acoustic signal transmitted by the implantable device at different adjusted positions within the body.

6. The implant assist device of claim 3, wherein the portion of the implant assist device that is an implantable device further comprises at least one acoustic transducer adapted to transmit an acoustic signal to the implantable device.

7. The implant assist device of claim 6, wherein the transmitted acoustic signal to the implantable device may be used to one of program or alter the operation of the implanted device.

8. The implant assist device of claim 1, wherein the implantation location is determined based on the one or more parameters associated with the acoustic signal transmitted by the implantable device.

9. A method for evaluating an acoustic communication link between an implantable device and an implant assist device, comprising:
    establishing an acoustic communication link between the implantable device and the implant assist device, the implant assist device including an acoustic transducer configured to receive an acoustic signal transmitted by the implantable device and circuitry configured to evaluate a performance of the acoustic communication link;
    comparing the performance of the acoustic communication link between the implant assist device and the implantable device based at least in part on a weighted sum of a plurality of parameters associated with the acoustic signal against a predetermined set of signal criteria; and
    providing information to a user interface indicating the performance of the acoustic communication link and a signal status and quality of the acoustic communication link for determining whether an implantation location is acceptable.

10. The method of claim 9, wherein establishing an acoustic communication link between the implantable device and the implant assist device includes transmitting the acoustic signal while the implantable device is at least partially disposed within an interior lumen of a delivery catheter.

11. The method of claim 9, wherein evaluating the performance of the acoustic communication link includes evaluating a signal strength and quality of the acoustic signal received by the implant assist device.

12. The method of claim 9, wherein evaluating the performance of the acoustic communication link includes evaluating at least one of a noise floor level parameter, carrier frequency parameter, signal timing parameter, signal duration parameter, signal morphology parameter, receiver gain parameter, receiver threshold parameter, carrier frequency parameter, decode ratio parameter, bit error rate parameter, bit correction rate parameter, an acoustic dampening parameter, and wake-up threshold margin parameter.

13. The method of claim 9, wherein the one or more parameters includes signal amplitude, and where evaluating the performance of the acoustic communication link includes comparing the amplitude of the acoustic signal against a threshold amplitude value.

14. The method of claim 9, further comprising adjusting a pulse count or pulse duration of the acoustic signal transmitted by the implantable device, and wherein evaluating the performance of the acoustic communication link includes evaluating a response of the acoustic signal to the adjusted pulse count or pulse duration.

15. The method of claim 9, further comprising adjusting a clock frequency of the acoustic signal, and wherein evaluating the performance of the acoustic communication link includes measuring a clock skew associated with the implanted device.

16. The method of claim 9, wherein establishing an acoustic communication link includes transmitting a first acoustic signal from the implant assist device to the implantable device and receiving a second acoustic signal from the implantable device, wherein the second acoustic signal received from the implantable device is proportional in amplitude to the first acoustic signal.

17. The method of claim 9, further comprising adjusting a position of the implantable device based on the one or more parameters associated with the acoustic signal.

18. The method of claim 17, wherein the position of the implantable device is adjusted by at least one of moving or rotating a delivery catheter within the body based on feedback from the user interface.

* * * * *